United States Patent [19]

Weissman

[11] Patent Number: 4,697,700
[45] Date of Patent: Oct. 6, 1987

[54] PROTECTIVE DEVICE FOR DENTAL MODELS

[76] Inventor: Bernard Weissman, 225 E. 48th St., New York, N.Y. 10019

[21] Appl. No.: 765,673

[22] Filed: Aug. 15, 1985

[51] Int. Cl.⁴ ............................................. A60C 19/10
[52] U.S. Cl. .................................... 206/83; 206/63.5; 206/467; 206/470; 433/34
[58] Field of Search ................. 206/83, 461, 463, 467, 206/470, 480, 490, 557, 562, 563, 525, 63.5; 433/34, 60; 249/54; 220/334, 339

[56] References Cited

U.S. PATENT DOCUMENTS

| 2,102,643 | 12/1937 | Pellegrini | 206/83 |
|---|---|---|---|
| 2,375,645 | 5/1945 | Gordon | 206/83 |
| 2,444,294 | 6/1948 | Jones | 206/83 |
| 2,565,899 | 8/1951 | Wilcox | 206/83 |
| 2,620,919 | 12/1952 | Passmore | 206/83 |
| 3,365,308 | 7/1964 | Janicke | 206/525 |
| 3,645,384 | 2/1972 | Wind | 220/339 |
| 3,710,975 | 1/1973 | Jansen | 220/339 |
| 4,059,902 | 11/1977 | Shiokawa | 433/34 |
| 4,116,416 | 9/1978 | Segura | 433/34 |
| 4,119,292 | 10/1978 | Haker | 249/54 |
| 4,158,915 | 6/1979 | Stengel | 433/60 |
| 4,283,173 | 8/1981 | Browne et al. | 433/34 |
| 4,439,151 | 3/1984 | Whelan | 433/60 |
| 4,494,934 | 1/1985 | Hoffman | 249/54 |
| 4,538,987 | 9/1985 | Weissman | 249/54 |
| 4,556,147 | 12/1985 | Mangnussen, Jr. | 206/525 |
| 4,605,127 | 8/1986 | Mangussen, Jr. | 206/525 |

Primary Examiner—Stephen Marcus
Assistant Examiner—David T. Fidei
Attorney, Agent, or Firm—Goodman & Teitelbaum

[57] ABSTRACT

A protective device for holding a dental model which is used in producing a dental prosthesis, the protective device including an arcuate tray having a substantially flat base wall with a continuous peripheral side wall upstanding therefrom so as to define a cavity chamber therein for receiving a correspondingly shaped arcuate pedestal of the dental model which can be securely seated therein. In one embodiment, the tray supports the dental model during machining of the model. In another embodiment, the tray forms part of a carrier having a cover portion which is hinged onto the tray portion so as to define therebetween a compartment for receiving the dental model. The tray can be keyed to accommodate specific keyed portions molded into the dental model.

3 Claims, 13 Drawing Figures

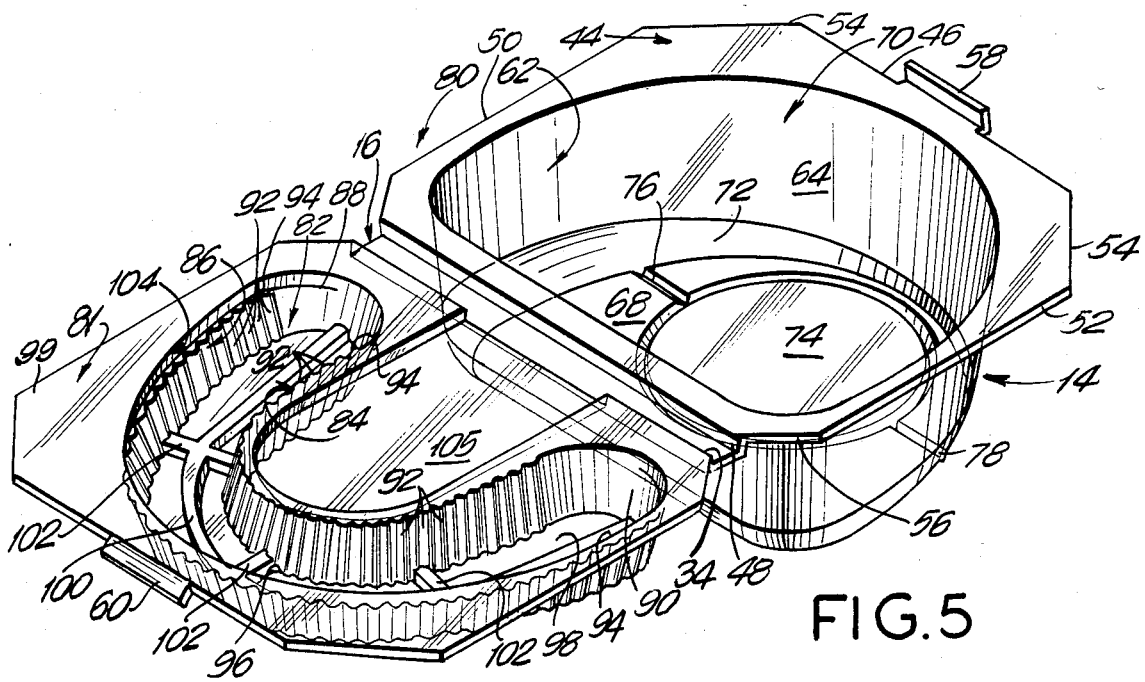
FIG.5
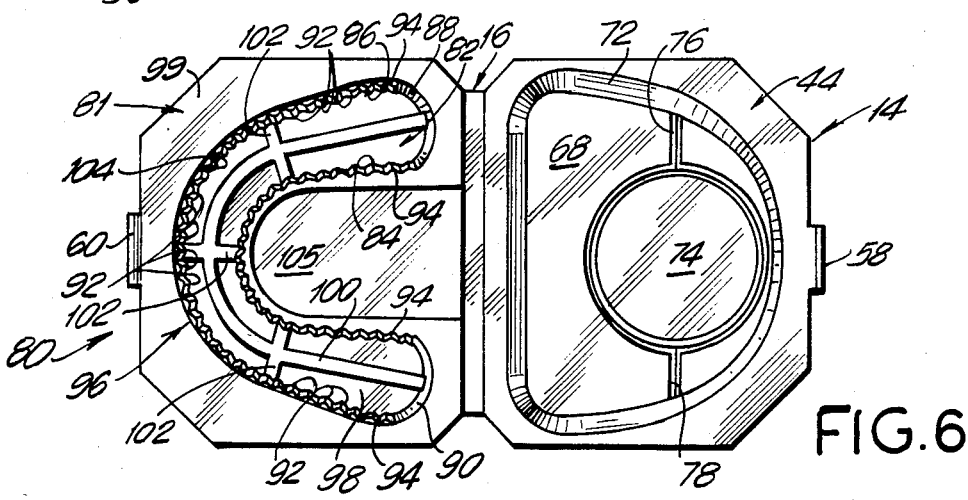
FIG.6
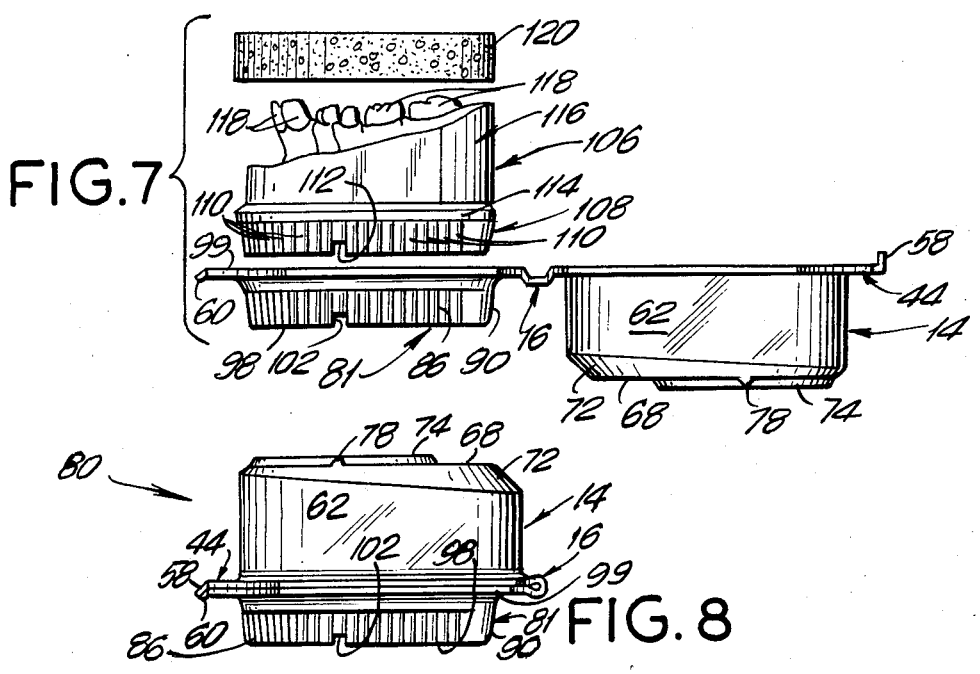
FIG.7
FIG.8

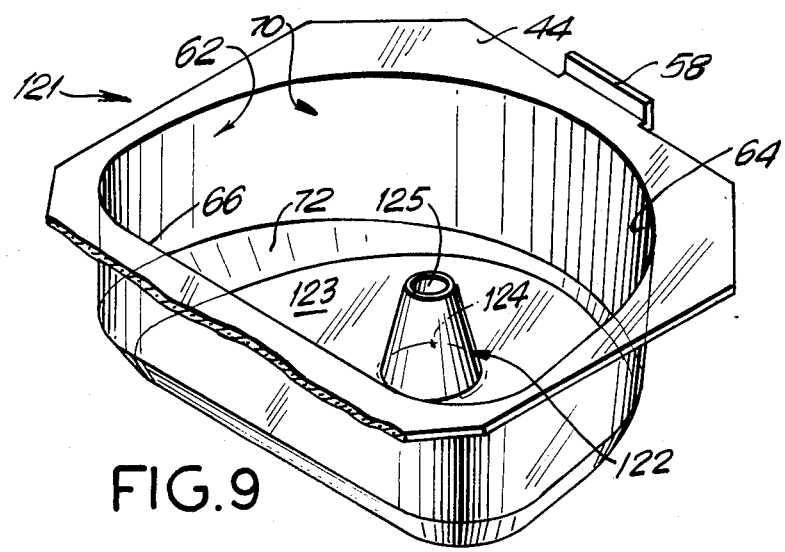
FIG.9
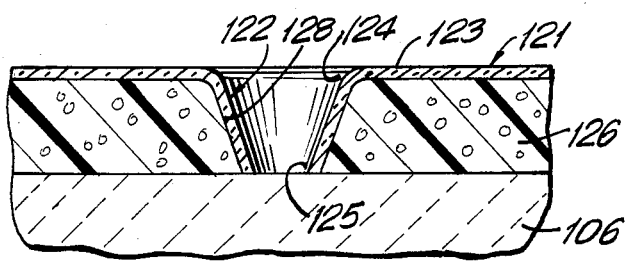
FIG.10
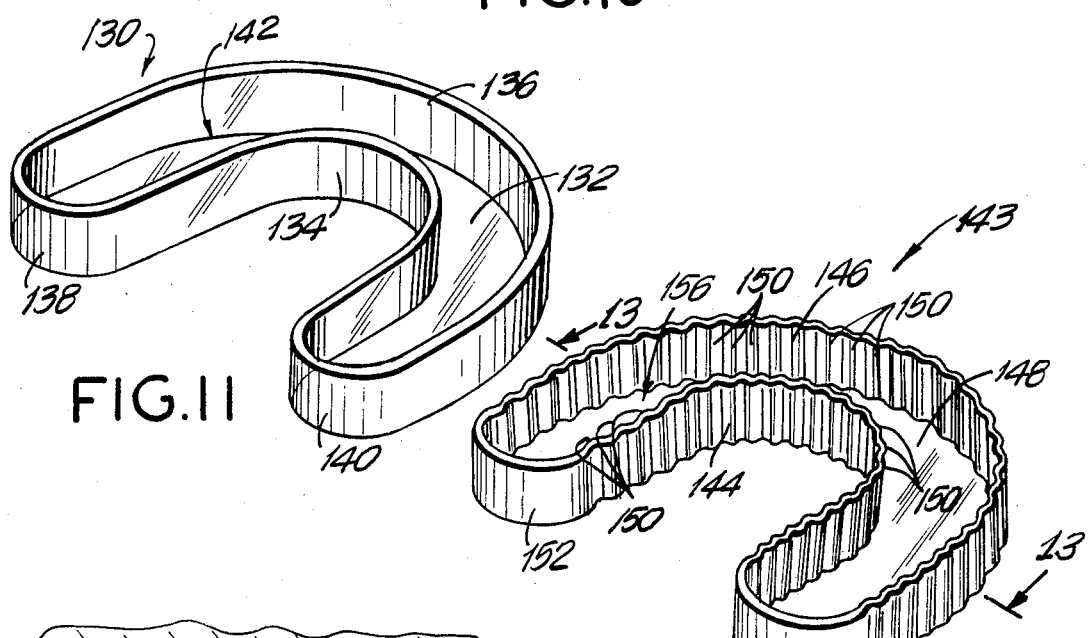
FIG.11
FIG.12
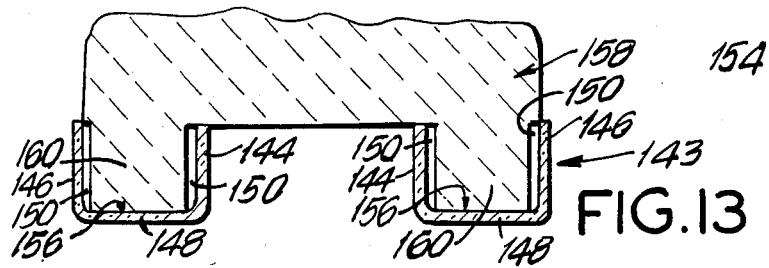
FIG.13

PROTECTIVE DEVICE FOR DENTAL MODELS

BACKGROUND OF THE INVENTION

This invention relates to dental accessories, and more particularly to a protective device for holding a dental model to aid in the transport, storage, and sectioning of the dental model.

In connection with the production of tooth crowns, tooth bridges, and the like, it is general procedure to form a mold which is used as a model base in the formation of a dental prosthesis. The dental model is generally produced in a die tray and includes an imprint in which the prepared teeth as well as possibly the gum, mandible portions, palate, etc., are imprinted. The completed dental model is then typically cut into sections for producing the dental prosthesis or portions thereof.

After the dental model has been formed, it must be transported, stored, shipped, or in some way moved between the laboratory and the dentist. The dental model is usually formed out of stone-like material and is subject to cracking and chipping which causes great hardship and cost since the entire procedure must be repeated at an additional expenditure of time for the dentist, the patient and the laboratory. Transporting or moving the dental model exposes it to the risk of being damaged.

Additionally, after the dental model has been prepared, it is typically machined, by either drilling or cutting, before producing the dental prosthesis. During such machining operation, the dental model must be carefully handled and securely retained in place, or the model may be damaged.

Accordingly, there is need of protective devices which can hold the dental model during storage and transport, as well as retaining the dental model during the machining thereof.

In many cases, during the formation of the dental model, specific imprints or keys will be formed into the dental model so that the repositioning of the dental model back into the die tray will provide the proper orientation. For example, specified corrugations or teeth may be formed into the pedestal portion of the dental model in a unique configuration so as to ensure the proper reinsertion thereof back into the die tray. Other types of key arrangements can also be formed into the dental model for such purposes.

The transport or storage tray which securely retains the dental model must accordingly accommodate such keyed portions which are formed into the dental model or its pedestal portion to permit proper seating of the dental model, thereby avoiding damaging the model.

SUMMARY OF THE INVENTION

Accordingly, it is an object of the present invention to provide a protective device for holding a dental model which dental model is used in the production of a dental prosthesis.

Another object of the present invention is to provide a protective device for a dental model, wherein the protective device is in the form of a carrier tray which can be used for supporting the dental model during the storage and transport thereof.

Yet a further object of the present invention is to provide a protective device for holding a dental model during the machining thereof.

Still another object of the present invention it to provide a protective device for holding a dental model, which protective device includes a tray portion and a hinged cover portion defining therebetween a compartment in which the dental model is securely seated.

A further object of the present invention is to provide a protective device for holding a dental model, which protective device includes a tray portion having a keyed seat which matingly receives an appropriately keyed pedestal portion of a dental model.

Another object of the present invention is to provide a protective device for holding a dental model, which protective device can securely hold the dental model for storage and transport thereof so as to avoid the possibility of any cracking or chipping of the dental model.

Briefly, in accordance with the present invention, there is provided a protective device for holding a dental model, which model is used in producing a dental prosthesis. The protective device includes an arcuate tray having a substantially flat base wall and a contiguous peripheral side wall upstanding from the base wall. The base and side walls define a cavity chamber for receiving the correspondingly shaped arcuate pedestal of a dental model, which model can be securely seated in the tray.

In one embodiment of the present invention, the protective device forms an arcuate support tray in which the dental model can be inserted during the machining thereof. The arcuate support tray can include appropriate keying arrangements to matingly receive correspondingly keyed portions on the dental model, such as on its pedestal portion in order to tightly retain the dental model when seated in the tray.

In another embodiment, the protective device comprises a carrier having a lower tray portion with a hinged upper cover portion. The tray portion includes the cavity chamber and a mating recessed chamber is formed in the cover portion, which together define a compartment in which the dental model is securely retained.

The protective device can be formed of a one piece integral construction fabricated out of plastic material so as to permit the viewing of the dental model within the protective device. A space can be provided on the protective device. A space can be provided on the protective device for placing an appropriate legend identifying the patient, doctor, or other indicia identifying the particular dental model contained in the protective device. Flange portions extend outwardly from the engaging portions of the upper cover and lower tray of the protective device to form a protective bumper or spacer around the dental model disposed within the protective device for absorbing shocks and preventing damage to the dental model.

BRIEF DESCRIPTION OF THE DRAWINGS

With the above and additional objects and advantages in view, as will hereinafter appear, this invention comprises the devices, combinations, and arrangements of parts hereinafter described, by way of example, and illustrated in the accompanying drawings of a preferred embodiment in which:

FIG. 5 is a perspective view similar to that shown in FIG. 1, showing another embodiment of the protective carrier tray in which the chamber in the lower tray portion has a substantially U-shaped configuration with appropriately keyed arrangements for receiving a correspondingly keyed pedestal portion of the dental model;

FIG. 6 is a top view of the opened carrier tray shown in FIG. 5;

FIG. 7 is a side elevational view of the opened carrier tray shown in FIG. 5, showing the dental model positioned for placement into the lower tray portion together with a foam pad to hold the dental model in place within the carrier tray;

FIG. 8 is a side elevational view showing the carrier tray of FIG. 5 in its closed position;

FIG. 9 is a fragmented perspective view of another embodiment of the upper cover portion showing a frustroconical holding member depending from the top wall of the cover portion for restraining the dental model within the carrier tray;

FIG. 10 is a partial cross section view taken through the cover portion of FIG. 9, showing the positioning of the frustroconical holding member with respect to a foam padding and the dental model;

FIG. 11 is a perspective view showing a protective device in the form of an arcuate support tray for holding the dental model during machining thereof;

FIG. 12 is a perspective view of another embodiment of the arcuate support tray similar to that shown in FIG. 11, showing a keyed portion for receiving a correspondingly keyed pedestal portion of the dental model; and FIG. 13 is a cross sectional view taken along lines 13—13 of FIG. 12, showing the positioning of a fragmented dental model within the arcuate support tray of FIG. 12.

In the various figures of the drawing, like reference characters designate like parts.

DESCRIPTION OF THE PREFERRED EMBODIMENTS

Figure 1:
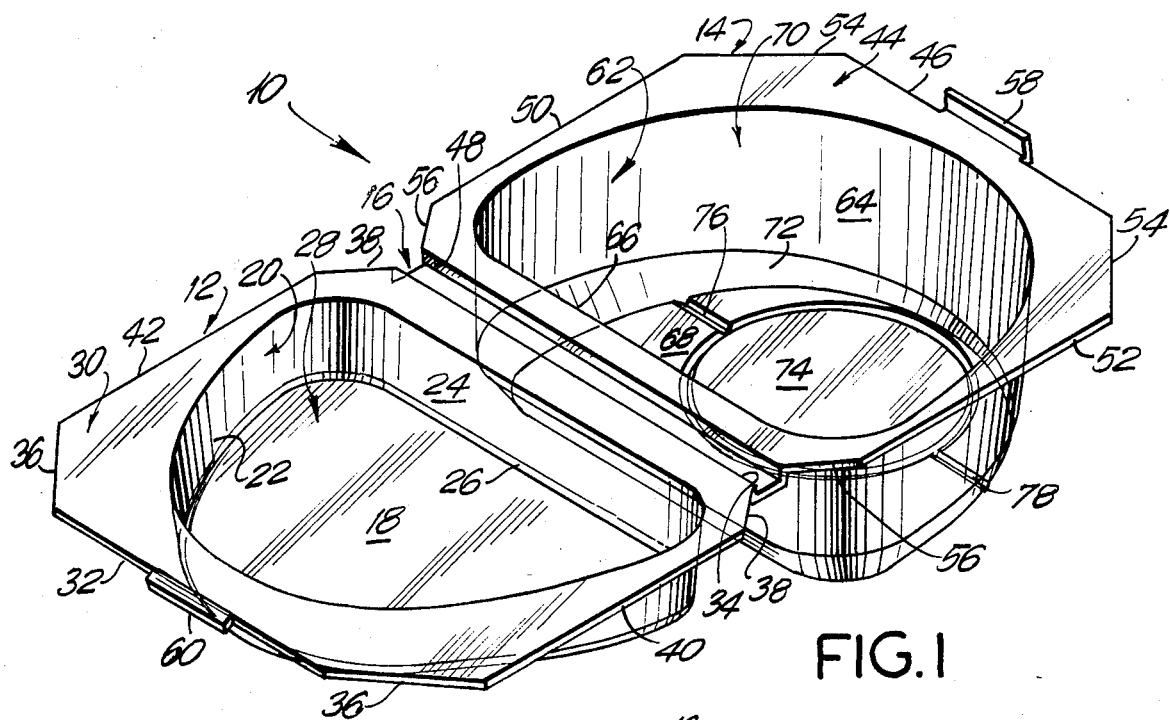
FIG. 1 is a perspective view of a protective carrier tray in its opened position, showing a lower tray portion hingedly connected to an upper cover portion to provide a compartment into which a dental model can be inserted.
Figure 2:
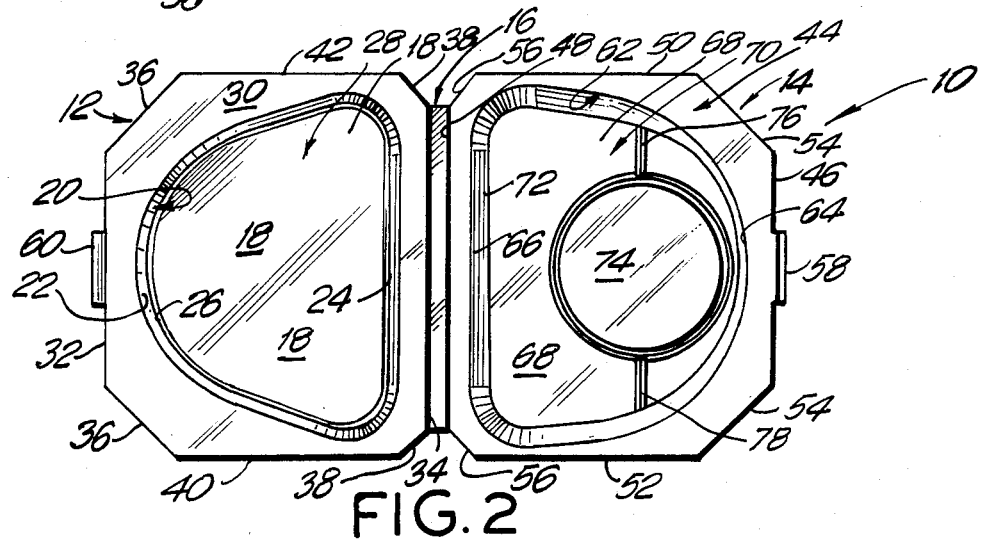
FIG. 2 is a top view of the opened carrier tray shown in FIG. 1.
Figure 3:
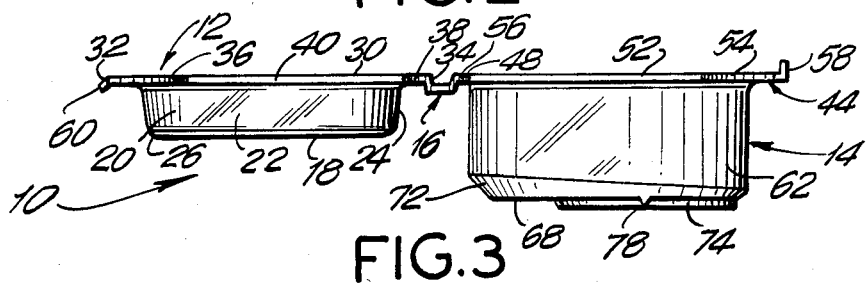
FIG. 3 is a side elevational view of the opened carrier tray shown in FIG. 1.

Referring now to FIGS. 1-4, there is shown a protective device in the form of a carrier tray 10 for holding a dental model, such dental model being of the type typically used in producing a dental prosthesis. The carrier tray 10 includes a lower tray portion 12 and an upper cover portion 14, which are hingedly secured together by means of an integral hinge 16. The carrier tray 10 is fabricated from plastic material, preferably being transparent.

The lower tray portion 12 includes a substantially flat base wall having approximately a semi-circular configuration. A continuous peripheral side wall 20 extends upwardly from the base wall 18 and includes an arcuate outer section 22 having a U-shaped configuration with its distal ends closed off by a continuous end wall 24. A beveled edge portion 26 is formed at the junction between the side and base walls. The base wall 18 and upstanding side walls 20 define a cavity chamber 28 in which the lower pedestal portion of the dental model can be inserted.

Flanging outward from the top edge of the side wall 20 is an upper wall 30 which is substantially flat and has a distal edge 32 and an opposing medial edge 34. For convenience, the side lateral portions of the distal edge 32 are inwardly tapered at 36, being interconnected to the medial edge 34 by substantially straight side edges 40, 42 which are connected to the inwardly tapered portions 38 of the medial edge 32, respectively. Preferably the side wall 20 is tapered inwardly from the upper wall 30 to the base wall 18, as shown best in FIGS. 3 and 4.

Figure 4:
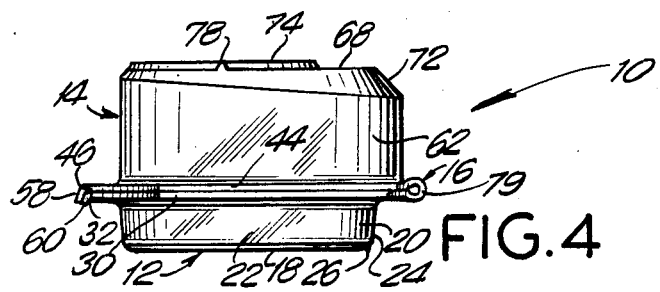
FIG. 4 is a side elevation view showing the carrier tray in its closed position.

The upper cover portion 14 includes a flat facial wall 44 having substantially an identical peripheral configuration as the upper wall 30 of the lower tray portion 12. Specifically, the facial wall 44 includes a distal edge 46, a medial edge 48, opposing side edges 50, 52, and angled forward and rear edges 54, 56 interconnecting the distal and medial edges 46, 48 with the side edges 52, 54 respectively. The integral hinge 16 extends between the two medial edges 34, 48. An appropriate latch arrangement is provided for the opposing distal edges 46, 32. Specifically, an outwardly vertically directed tab 58 is provided at the distal edge 46 which extends downwardly over a forward lip 60 formed at the distal edge 32, so as to latch the cover portion 14 onto the tray portion 12 in a closed position of the carrier tray as shown in FIG. 4.

Extending from the facial wall 44 is an outer wall 62 including an arcuate U-shaped section 64 with its distal ends closed off by a continuous end wall 66. A top wall 68, having approximately a semi-circular configuration, closes off the outer wall 62 and together therewith defines a recessed chamber 70. A bevelled edge portion 72 is provided at the junction between the outer wall 62 and the top wall 68.

The outer configuration of the recessed chamber 70 formed in the upper cover portion 14 substantially conforms to the outer configuration of the cavity chamber 28 formed in the lower tray portion 12. When the upper cover portion 14 closes onto the lower tray portion 12, the two chambers 70, 28 confrontingly mate with the facial wall 44 engaging the upper wall 30, so as to define an enclosed compartment within the closed carrier tray 10, as shown in FIG. 4, in which the dental model can be securely retained.

Top wall 68 includes a raised boss 74 on which can be provided identification indicia indicating the doctor, patient, manufacturer and like information. A pair of ribs 76, 78 laterally extend from the boss 74 for supporting the top wall 68.

Integral hinge 16 has substantially a U-shaped configuration so that in the closed position, as shown in FIG. 4, a loop 79 is formed to facilitate opening and closing of the cover portion 14 onto the tray portion 12.

With the arrangement as shown, a dental model can be easily seated into the cavity chamber 28 of the lower tray portion 12. The cover position 14 can then be closed onto the tray portion 12 and secured together with the latch arrangement 58, 60 to securely retain the dental model therein, thus permitting the transport and storage of the dental model without risking any cracking or chipping of the dental model. Whenever desired, the carrier tray 10 can be opened and the dental model can be easily removed therefrom for further operation thereon in the formation of the dental prosthesis.

In many cases, particular keyed arrangements are directly molded into the dental model so that the dental model can only be re-inserted back into the die tray in a particular orientation. Where a keyed arrangement is provided in the dental model, the carrier tray of the present invention can be modified to include a correspondingly keyed seat so that the dental model will securely fit into the modified tray by means of the keyed arrangement.

By way of example, a keyed arrangement for a dental model is described in copending U.S. patent Ser. No. 534,812 filed on Sept. 22, 1983 by the present inventor, entitled "DENTAL DIE TRAY ASSEMBLY", now U.S. Pat. No. 4,538,987. In such application, there is described a dental die tray which includes a keyed arrangement having a plurality of corrugations, teeth or ribs, which will be cast directly into the pedestal portion of the dental model. A mating keyed arrangement can therefore be included into the dental carrier tray of the present invention.

Specifically, referring to FIGS. 5-8, there is provided a modified carrier tray 80 which includes keyed portions specifically designed to conform to the configuration of a dental model formed in accordance with the aforementioned copending patent application. The protective carrier tray 80 is substantially similar to that shown in FIGS. 1-4, except that the cavity chamber formed in the lower tray portion is redesigned to include the specific mating keyed arrangement. Accordingly, all parts of the protective carrier tray 80 of FIGS. 5-8 are identified identically as those in FIGS. 1-4, particularly the upper cover portion 14 and the integral hinge 16, with the exception of the cavity chamber portion in the lower tray portion.

The cavity chamber in the modified lower tray portion 81 is generally at 82, being arcuate in shape and including an inner wall 84 and an outer wall 86 interconnected at their respective ends by rounded interconnecting walls 88, 90 to provide a U-shaped configuration. The arcuate inner and outer walls 84, 86, include corrugations or teeth 92 which protrude into the cavity chamber 82. The teeth 92 are of uniform projection, but certain sets of teeth are wider than others. Specifically, the radius of the teeth at the distal ends 94 adjacent the interconnecting walls 88, 90 is larger than the radius of the teeth at the medial section 96. The cavity chamber 82 widens as it progresses from the lower surface, U-shaped base wall 98 to the upper wall 99 to form an outwardly flared cavity chamber whose upper end is wider than its lower end. The upper wall 99 is similar to the above mentioned upper wall 30 of the lower tray portion 12, except as mentioned below.

Formed at the bottom of the cavity chamber 82 and projecting upwardly from the lower wall 98 is an arcuate rib 100, being substantially U-shaped along the U-shaped base wall 98, and including a plurality of laterally extending reinforcing webs 102. Three webs 102 are shown which interconnect the inner and outer opposing walls 84, 86. The rib 100 has opposing side surfaces which are downwardly sloped. However, the two sloped side surfaces are at different angles and specifically, the outer slope facing wall 86 is steeper than the inner slope facing wall 84. The under surfaces of the rib 100 and the webs 102 are recessed, as indicated in FIGS. 7 and 8, which are formed in the molding thereof.

The outer wall 86 of the cavity chamber 82 is stepped just below the upper wall 99 to provide a recessed seat 104 peripherally formed in a U-shape about the outer wall of the cavity chamber 82 and spaced below the upper wall 99. A palate wall section 105 is formed between the leg portions of the inner wall 84 and extends to the hinge 16, the palate wall section 105 being stepped slightly below the upper wall 99.

As shown in FIG. 7, a dental model 106 is being inserted into the dental tray 80. The dental model 106 includes a lower pedestal portion 108 into which there has been molded teeth 110, web slots 112, a peripheral flange 114, and a U-shaped rib slot (not shown) to mating configurations formed in the lower tray portion 81 to accommodate these keyed portions. The upper part 116 of the dental model 106 includes the model teeth 118 which are used in producing the dental prosthesis, the model teeth 118 being formed in accordance with standard techniques well known in the dental art.

It should be appreciated, that the particular keyed configuration provided within the cavity chamber 82 accommodates the particular configuration described in the aforementioned copending application. However, should other types of keyed configurations be cast within the dental model, corresponding keyed configurations could matingly be formed in the lower tray portion. Additionally, the upper tray portion could likewise have particular keyed configurations should such be needed for a particular dental model being inserted into the carrier tray.

As shown in FIG. 7, there can additionally be included a piece of foam padding 120 which can fit over the upper surface of the dental model 106 and placed beneath the top wall 68 of the cover portion 14. The foam padding 120 fills the space between the dental model 106 and the top wall 68, and provides a tight fit of the dental model without damage thereto so that the dental model is prevented from moving within the carrier tray.

Referring now to FIGS. 9 and 10, a retaining post 122 is provided within a modified cover portion 121. The retaining post 122 is shown as a frustroconical member depending from a modified top wall 123 of the cover portion 121, and is opened at its top end 124 and bottom end 125. The lower end 125 of the frustroconical retaining post 122 can be cut at a proper desired length in order to fit onto the dental model to securely retain the dental model in the cover tray. Accordingly, all the other parts of the protective carrier tray are the same as mentioned above.

In FIG. 10, the dental model 106 is also retained in place by means of the foam pad. In order to accommodate the frustroconical retaining post 122, a modified foam pad 126 could include an opening 128 for receiving the retaining post 122 therethrough. Alternately, the foam padding or foam material could be placed around the retaining post 122 to retain the dental model in place.

As shown in FIG. 11, the protective device of the present invention can also be provided as a support tray 130. The support tray 130 includes a base wall 132 of substantially U-shaped configuration. Upstanding inner wall 134 and outer wall 136 are interconnected by rounded end walls 138, 140 to provide an internal cavity 142 defined between the base wall 132 and the upstanding peripheral walls 134, 136, 138, 140. The cavity 142 receives the pedestal or bottom portion of a dental model to securely retain it. Preferably, the support tray is fabricated from a transparent plastic material.

While retained within the support tray 130, the model can then be machined, such as by cutting, drilling and the like. For example, a drilling operation is described in U.S. Pat. No. 3,941,496, issued to the inventor of the present application on Mar. 2, 1976, entitled "Drilling Machine For Plastic Casts or Models." Other machining operations or dental models are well known in the art.

Normally, when machining or handling dental models, there is a possibility that it may crack or break, particularly when coming in contact with a hard surface, such as the work table of drilling or cutting machines. Accordingly, the support tray 130 would now contact the work table during such operations, where the plastic material of the support tray 130 can easily be cut or drilled through as required by the particular operation being performed on the dental model.

The support tray can also be modified to include appropriate keyed arrangements in order to accommodate particular keyed portions formed in the dental model. As shown in FIG. 12, the modified support tray 143 includes inner and outer walls 144, 146 upstanding from the base wall 148, the inner and outer walls 144, 146 being provided with teeth 150. Smooth rounded end walls 152, 154 complete the U-shaped configuration of the support tray 143. A dental model would be seated in the cavity 156 provided between the upstanding peripheral walls and the base wall. The teeth 150 would conform to the molded teeth in the lower pedestal portion of the dental model. The teeth 150 can include the appropriate arrangement and configuration heretofore described in connection with the teeth 92, shown with FIG. 5. Accordingly, ribs, webs, etc., could also be provided, as required. A particular dental model 158 would then be inserted into the support tray 143, as shown in FIG. 13, so that the lower pedestal portion 160 is seated in the cavity 156. Thus, the dental model 158 is now protected to avoid damage thereof when being placed on a work table having a hard surface, where the support tray 143 will now come in contact with the work table surface.

There has been disclosed heretofore the best embodiment of the invention presently contemplated. However, it is to be understood that the present disclosure relates to preferred embodiments of the present invention which are for purposes of description only and are not to be construed as a limitation of the present invention.

I claim:

1. In a protective carrier for holding and protecting a dental model used in producing a dental prosthesis, said carrier being an integral one-piece construction of plastic material and consisting of a tray portion, a cover portion, a hinged portion connecting said tray portion to said cover portion and latch means for securing said tray portion and said cover portion together said tray portion having a cavity chamber for receiving a correspondingly shaped pedestal portion of the dental model, said cover portion having a recessed chamber for covering an upper part of the dental model, said recessed chamber and said cavity chamber providing a closed compartment for securely retaining the dental model during transport and storage thereof, said tray portion having a substantially U-shaped planar configuration with said cavity chamber having a U-shaped base wall and upstanding U-shaped facing outer and inner cavity walls interconnected by rounded end walls, an improvement comprising:

keyed means provided in said cavity chamber of said tray portion for matingly engaging keyed portions provided on the pedestal portion of the dental model, said keyed means including:

continuous teeth disposed on said facing outer and inner cavity walls, said teeth extending into said cavity chamber to mate with teeth provided on the pedestal portion of the dental model;

said teeth on said inner cavity wall having a greater height from said base wall than said teeth on said outer cavity wall to provide a U-shaped recessed seat about an upper portion of said outer cavity wall to receive a peripheral flange of the pedestal portion of the dental model;

a U-shaped rib projecting from said base wall into said cavity chamber to be received in a U-shaped slot provided in a bottom part of the pedestal portion of the dental model, said rib extending from one rounded end wall of the cavity chamber to the other rounded end wall; and web means extending upwardly from said base wall and laterally from said outer cavity wall to said rib and then to said inner cavity wall for supporting said rib and for being received in mating web slots provided in the bottom part of the pedestal portion of the dental model;

a resilient pad for positioning within said recessed chamber to retain the dental model securely in place within said closed compartment; and retaining post means projecting into said recessed chamber for pressing onto the upper part of the dental model to hold the dental model in place, said resilient pad including an aperture for receiving said retaining post means therethrough.

2. A protective carrier as in claim 1, wherein said latch means include an outwardly vertically directed tab provided at a distal edge of said cover portion for downward engagement over a forward lip provided at a distal edge of said tray portion.

3. A protective carrier as in claim 1, wherein said teeth on said outer and inner cavity walls are larger adjacent to said rounded end walls than at a medial bite section of said cavity chamber.

* * * * *